United States Patent

Yoshimura et al.

[11] Patent Number: 6,147,058
[45] Date of Patent: Nov. 14, 2000

[54] 1-(2-DEOXY-2-FLUORO-4-THIO-BETA-D-ARABINOFURANOSYL)CYTOSINE

[75] Inventors: Yuichi Yoshimura, Kashima-gun; Kenji Kitano, Choshi; Shinji Miura, Choshi; Haruhiko Machida, Choshi; Mikari Watanabe, Choshi, all of Japan

[73] Assignee: Yamasa Corporation, Japan

[21] Appl. No.: 08/973,529

[22] PCT Filed: Apr. 9, 1997

[86] PCT No.: PCT/JP97/01206

§ 371 Date: Jun. 29, 1998

§ 102(e) Date: Jun. 29, 1998

[87] PCT Pub. No.: WO97/38001

PCT Pub. Date: Oct. 16, 1997

[30] Foreign Application Priority Data

Apr. 9, 1996 [JP] Japan ................................... 8-111968
Jul. 26, 1996 [JP] Japan ................................... 8-215082
Sep. 30, 1996 [JP] Japan ................................... 8-278631

[51] Int. Cl.[7] .......................... A61K 31/70; C07H 19/09; C07H 19/10; C07H 1/00
[52] U.S. Cl. .............................. 514/49; 514/51; 536/55.3; 536/28.5; 536/26.1
[58] Field of Search ................................. 536/55.3, 28.5, 536/26.1; 514/49, 51

[56] References Cited

FOREIGN PATENT DOCUMENTS 8-53490  2/1996  Japan.
WO91/04982  4/1991  WIPO.
WO96/01834  1/1996  WIPO.

OTHER PUBLICATIONS

Jeong et al., Chemistry Letters, pp. 301–302, 1995.
Jeong et al., Tetrahedron Letters, 35(41):7569–7572, 1994.
Jeong et al., Tetrahedron Letters, 35(41):7573–7576, 1994.
Y. Yoshimura et al., *Nucleic Acids Symposium Series*, No. 35, pp. 15–16 (1996).
Y. Yoshimura et al., *Journal of Organic Chemistry*, vol. 61, No. 3, pp. 822–823 (1996).

*Primary Examiner*—Gary L. Kunz
*Attorney, Agent, or Firm*—Wenderoth, Lind & Ponack, L.L.P.

[57] ABSTRACT

The present invention relates to 1-(2-deoxy-2-fluoro-4-thio-beta-D-arabinofuranosyl)cytosines having excellent antitumor activity, represented by formula [I]:

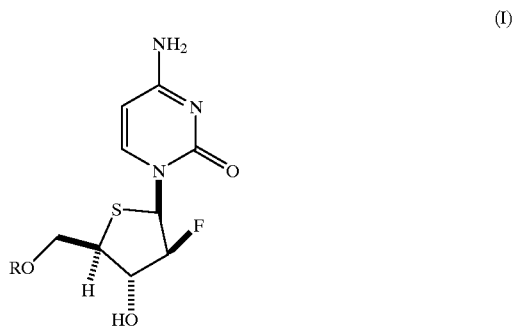

wherein R represents a hydrogen atom or a phosphoric acid residue, and to a process for the production and use thereof.

5 Claims, 2 Drawing Sheets

1-(2-DEOXY-2-FLUORO-4-THIO-BETA-D-ARABINOFURANOSYL)CYTOSINE

This application is a 371 of PCT/JP97/01206 filed Apr. 9, 1997.

TECHNICAL FIELD

The present invention relates to novel 1-(2-deoxy-2-fluoro-4-thio-beta-D-arabinofuranosyl)cytosines and a process for the production and use thereof.

BACKGROUND ART

A research group of University of Birmingham makes reference to 1-(2-fluoro-4-thio-beta-D-arabinofuranosyl)-5-methyluracil and 1-(2-fluoro-4-thio-beta-D-arabinofuranosyl)-5-iodocytosine in International Patent Application PCT/GB90/01518 (International Publication Number: WO 91/04982).

Further, a research group of NIH has recently made a report on such compounds as 1-(2,3-dideoxy-2-fluoro-4-thio-beta-D-erythro-pentafuranosyl)uracil represented by the following formula:

1a, b; W = X = Y = Z = H
2a, b; W = F, X = Y = Z = H
3a, b; X = F, W = Y = Z = H
4a, b; Y = F, W = X = Z = H
5a, b; Z = F, W = X = Y = H provided that B is uracil in series a, and cytosine in series b (Tetrahedron Letters, 35, 7569–7572 (1994); Tetrahedron Letters, 35, 7573–7576 (1994); Chemistry Letters, 301–302 (1995)).

However, the group of University of Birmingham describes the above two compounds as mere instances, and fails to show examples in which they were practically synthesized. Moreover, although a process for producing the compounds is explained in the specification for the aforementioned international patent application, the process is simply an application of those processes which are described in known references (*J. Org. Chem.*, 50, 2597 (1985), *J. Org. Chem.*, 50, 3644 (1985)). It is clear from the above-described reports made by the group of NIH that desired compounds can never be obtained by employing such a process. The specification for the foregoing international application slightly makes mention of the antiviral activity of the compounds, but is quite silent on specific data in terms of the activity.

Further, although the group of NIH makes reference to the anti-HIV activity of the compounds synthesized, the activity is not necessarily satisfactory.

Furthermore, both of the groups have made no report on other biological activities than antiviral activity.

DISCLOSURE OF THE INVENTION

We formerly developed a simple process for synthesizing 2'-deoxy-2'-substituted-4'-thionucleoside derivatives, using glucose as a starting material (WO 96/01834). After this, we continued our studies on the basis of knowledge acquired in the course of the development of this process. As a result, we have established a simple process for synthesizing 2'-deoxy-2'-fluoro-4'-thioarabinonucleosides, and synthesized various compounds by using this new process. In the process of testing the biological activities of the compounds synthesized, we have found that especially 1-(2-deoxy-2-fluoro-4-thio-beta-D-arabinofuranosyl)cytosines have excellent antitumor activity. The present invention has been accomplished on the basis of this finding.

The present invention therefore relates to 1-(2-deoxy-2-fluoro-4-thio-beta-D-arabinofuranosyl)cytosines represented by the following formula [I]:

wherein R represents a hydrogen atom or a phosphoric acid residue, and to pharmaceutical compositions, especially antitumor agents, comprising these compounds as active ingredients.

Further, the present invention also relates to a process for producing 1-(2-deoxy-2-fluoro-4-thio-beta-D-arabinofuranosyl)cytosines represented by the above formula [I], comprising the following 1st to 3rd steps:

1st step:
a step of reacting a compound represented by formula [II] with diethylaminosulfur trifluoride (DAST) after protecting the primary hydroxyl group of the compound [II], thereby obtaining a compound represented by formula [III]:

wherein $R_1$ and $R_2$ represent an alkyl, silyl or acyl group;

2nd step:
a step of converting the compound represented by formula [III] into a sulfoxide by reacting the compound [III] with an oxidizing agent, and subjecting the sulfoxide to Pummerer rearrangement reaction by treating it with an acid anhydride or acid chloride, thereby obtaining a compound represented by formula [IV]:

wherein $R_1$ and $R_2$ are as defined above, and $R_3$ represents an acyl group; and 3rd step:

a step of subjecting the compound represented by formula [IV] and $N^4$-acylcytosine or cytosine to glycosylation reaction in the presence of a Lewis acid catalyst to obtain a protected compound, removing the protecting groups, and, if desired, phosphorylating the 5'-position of the sugar moiety of the compound, thereby obtaining a 1-(2-deoxy-2-fluoro-4-thio-beta-D-arabinofuranosyl)cytosine represented by formula [I]:

wherein R, $R_1$, $R_2$ and $R_3$ are as defined above.

Furthermore, the present invention relates to a process for producing 1-(2-deoxy-2-fluoro-4-thio-beta-D-arabinofuranosyl)cytosines represented by the above formula [I], comprising the following 1st to 4th steps:

1st step:

a step of introducing a leaving group into the hydroxyl group on a compound represented by formula [V], and treating the compound with a nucleophilic reagent by which a fluorine atom can be introduced, thereby obtaining a compound represented by formula [VI]:

2nd step:

a step of selectively deprotecting the isopropylidene group at the 5- and 6-positions of the compound represented by formula [VI], selectively protecting the primary hydroxyl group of the compound, introducing a leaving group into the secondary hydroxyl group of the compound, deprotecting the primary hydroxyl group, performing 5,6-epoxidation, performing 5,6-thiiranation by using a sulfurizing reagent, opening the thiirane ring by using a nucleophilic reagent, and causing acylation, thereby obtaining a compound represented by formula [VII]:

wherein $R_4$ and $R_5$ represent an alkyl or acyl group;

3rd step:

a step of hydrolyzing the isopropylidene group at the 1- and 2-positions of the compound represented by formula [VII], carrying out oxidation by using an oxidizing agent, alkoxylating the 1-position of the compound, and protecting the hydroxyl group with a protecting group, thereby obtaining a compound represented by formula [VIII]:

wherein $R_4$ and $R_5$ are as defined above, $R_6$ and $R_7$ represent an alkyl or acyl group, and $R_8$ represents an alkyl group; and 4th step:

a step of brominating the alkoxy group at the 1-position of the compound represented by formula [VIII] by treating the compound [VIII] with a hydrogen bromide-acetic acid solution, subjecting the brominated compound and activated cytosine to glycosylation reaction to obtain a protected compound, removing the protecting groups, and, if desired, phosphorylating the 5'-position of the sugar moiety of the compound, thereby obtaining a 1-(2-deoxy-2-fluoro-4-thio-beta-D-arabinofuranosyl)cytosine represented by formula [I]:

wherein $R_6$, $R_7$ and $R_8$ are as defined above, and R represents a hydrogen atom or a phosphoric acid residue.

BEST MODE FOR CARRYING OUT THE INVENTION (1) Compounds of the Invention

The compounds of the present invention are 1-(2-deoxy-2-fluoro-4-thio-beta-D-arabinofuranosyl)cytosines represented by the above formula [I]. These compounds may also be in the form of salt, hydrate or solvate. Examples of the salts include pharmaceutically acceptable salts, for example, acid adducts such as hydrochlorides and sulfates when R is a hydrogen atom; and alkaline metal salts such as sodium, potassium and lithium salts, alkaline earth metal salts such as a calcium salt, and ammonium salts when R is a phosphoric acid residue.

Examples of the hydrates or solvates include those which are obtained by attaching 0.1 to 3.0 molecules of water or a solvent to one molecule of the compounds of the present invention or salts thereof. Further, various isomers such as tautomers can also be included in the compounds of the present invention.

(2) Process for Producing the Compounds of the Invention

The compounds of the present invention can be produced by a reaction process comprising the following 1st to 3rd steps.

1st step:

The 1st step is a step of reacting a compound represented by formula [II] with DAST after protecting the primary hydroxyl group of the compound [II], thereby obtaining a compound represented by formula [III]:

wherein $R_1$ and $R_2$ represent an alkyl, silyl or acyl group.

The starting compound is represented by the above formula [II], and can be readily synthesized from glucose by a known method (J. Org. Chem., 61, 822 (1996)).

$R_1$ and $R_2$ in the formula are as defined above. Specific examples of $R_1$ or $R_2$ include unsubstituted or substituted alkyl groups such as methyl, ethyl, benzyl, methoxybenzyl, dimethoxybenzyl, trityl and dimethoxytrityl, unsubstituted or substituted silyl groups such as t-butyldimethylsilyl and t-butyldiphenylsilyl, and acyl groups such as acetyl, benzoyl and pivaloyl.

The introduction of the protecting group can be achieved by a conventional technique. For example, in the case where a silyl protecting group is introduced, the reaction may be carried out by using 1 to 10 moles of a silylating agent (e.g., t-butyldiphenylsilyl chloride, t-butyldimethylsilyl chloride, or the like), and, when necessary, 1 to 5 moles of a base such as imidazole for 1 mole of the compound represented by formula [II], in a reaction solvent (e.g., a single solvent or solvent mixture of pyridine, picoline, dimethylaminiopyridine, dimethylformamide, acetonitrile, methylene chloride, or the like) at a temperature of 0 to 50° C.

The compound having a protecting group thus obtained is allowed to react with DAST to obtain a compound of formula [III].

The reaction with DAST can be carried out by using 1 to 20 moles of DAST for 1 mole of the compound of formula [II], in a solvent such as methylene chloride, dichloroethane, benzene, toluene, xylene, hexane or the like, at a temperature of −100 to 150° C., preferably −80° C. to room temperature, if necessary, in an atmosphere of an inert gas such as argon or nitrogen.

The compound of formula [III] may be isolated by a conventional means for the isolation and purification of sugar. For instance, it is possible to purify the reaction solution by silica gel column chromatography after it is partitioned between ethyl acetate and water, thereby isolating the compound [III].

2nd step:

The 2nd step is a step of converting the compound represented by formula [III] into a sulfoxide by reacting the compound [III] with an oxidizing agent, and subjecting the sulfoxide to Pummerer rearrangement reaction by treating it with an acid anhydride or acid chloride, thereby obtaining a compound represented by formula [IV]:

wherein $R_1$ and $R_2$ are as defined above, and $R_3$ represents an acyl group.

The derivation to a sulfoxide can be achieved by a conventional method. For instance, a method in which a compound is treated with m-chloroperbenzoic acid in methylene chloride at a temperature of −100 to 0° C. under a stream of an inert gas such as argon or nitrogen (J. Org. Chem., 61, 822 (1996)), or a method in which a compound is treated with sodium metaperiodate in an alcohol solvent such as methanol (Tetrahedron Letter, 993 (1979)) can be utilized.

The Pummerer rearrangement reaction, which is performed by a treatment with an acid anhydride or acid chloride, can also be carried out by a conventional method. Namely, the reaction can be carried out by using an acid anhydride such as acetic anhydride or trifluoroacetic anhydride, or an acid chloride such as mesyl chloride in an amount of 1 to 100 moles for 1 mole of the sulfoxide, at a temperature of −80 to 150° C., when necessary, under a stream of an inert gas such as argon or nitrogen. Although the acid anhydride or acid chloride used functions as a reaction solvent, it is also possible to carry out the above reaction in an organic solvent such as methylene chloride, when necessary.

The compound of formula [IV] thus obtained may be isolated by a conventional means for the isolation and purification of sugar. For instance, it is possible to purify the reaction solution by silica gel column chromatography after it is partitioned between ethyl acetate and water, thereby isolating the compound [IV].

3rd step:

The 3rd step is a step of subjecting the compound represented by formula [IV] and $N^4$-acylcytosine or cytosine to glycosylation reaction in the presence of a Lewis acid catalyst to obtain a protected compound, removing the protecting groups, and, if desired, phosphorylating the 5'-position of the sugar moiety of the compound, thereby obtaining a 1-(2-deoxy-2-fluoro-4-thio-beta-D-arabinofuranosyl)cytosine represented by formula [I]:

wherein $R_1$, $R_2$, $R_3$, and R are as defined before.

The glycosylation reaction of the compound of formula [IV] can be carried out by using 1 to 10 moles of $N^4$-acylcytosine or cytosine and 0.1 to 10 moles of a Lewis acid such as trimethylsilyl trifluoromethanesulfonate, tin tetrachloride, titanium tetrachloride, zinc chloride or boron trifluoride for 1 mole of the compound of formula [IV], in a solvent such as methylene chloride, chloroform, dichloroethane, acetonitrile or dimethylfor-mamide, at a temperature of −50 to 100° C., when necessary, under a stream of an inert gas such as argon or nitrogen.

The removal of the protecting group may be attained by a technique properly selected, depending upon the type of the protecting group used, from conventional techniques such as acid hydrolysis, alkali hydrolysis, a treatment with tetrabutylammonium fluoride, and catalytic hydrogenation For example, in the case where a benzyl protecting group is removed, deprotection can be attained by a method in which the compound is treated with boron trichloride or boron tribromide in methylene chloride at a temperature of −100° C. to room temperature under a stream of an inert gas such as argon or nitrogen.

Further, when a compound of formula [I] in which R is a phosphoric acid residue is synthesized, the desired compound of free acid type or salt type can be obtained by a conventional method, by reacting the compound which has been deprotected by the above method with a phosphorylating agent used for a conventional reaction for selectively phosphorylating the 5'-position of nucleosides, such as phosphorus oxychloride, tetrachloropyrophosphoric acid or beta-cyanoethylphosphoric acid-DCC.

The compound of the present invention thus obtained can be isolated and purified by a technique which is a proper combination of techniques conventionally used for the isolation and purification of nucleosides or nucleotides. For instance, in the case of the isolation of a nucleoside derivative (where R in formula [I] is a hydrogen atom), the desired compound may be obtained by crystallization from a proper solvent such as ethanol, which is carried out after the solvent in the reaction solution is distilled off. The desired compound can also be obtained as a salt-type compound, if necessary. Further, in the case of the isolation of a nucleotide derivative (where R in formula [I] is a phosphoric acid residue), the reaction solution may be purified by ion-exchange column chromatography, or adsorption column chromatography using activated carbon or the like, and then freeze-dried or crystallized to obtain the desired compound of free acid type. If necessary, the desired compound can also be obtained as a salt-type compound.

Alternatively, the compounds of the present invention can also be produced by a process comprising the following 1st to 4th steps. This process is advantageous in that the reaction conditions to be employed are relatively mild and that improvements in the reaction yield and in the yield of a beta-derivative can be attained or expected.

1st step:

The 1st step is a step of introducing a leaving group into the hydroxyl group on a compound represented by formula [V], and treating the compound with a nucleophilic reagent by which a fluorine atom can be introduced, thereby obtaining a compound represented by formula [VI]:

The starting compound is represented by formula [V], and can be readily produced from glucose by a known method (*Carbohydr. Res.*, 24, 192 (1972)).

Examples of the leaving group to be introduced include sulfonyl groups such as methanesulfonyl, p-toluenesulfonyl, benzenesulfonyl, imidazoylsulfonyl and trifluoromethanesulfonyl. Methanesulfonyl, p-toluenesulfonyl and imidazoylsulfonyl are preferred.

The introduction of the leaving group may be achieved by a conventional technique. For instance, in the case where methanesulfonyl, p-toluenesulfonyl or imidazoyl sulfonyl group is introduced, the reaction can be carried out by using 1 to 10 moles of methanesulfonyl chloride, p-toluenesulfonyl chloride or sulfuryl chloride, and, when necessary, 2 to 50 moles of a base such as imidazole for 1 mole of the compound of formula [V], in a reaction solvent (e.g., a single solvent or solvent mixture of pyridine, picoline, dimethylaminopyridine, dimethylformamide, acetonitrile, methylene chloride or the like), at a temperature of −50 to 50° C., preferably 0 to 50° C.

As the nucleophilic reagent by which a fluorine atom can be introduced, potassium fluoride (including a spray-dried product), potassium hydrogenfluoride, ammonium fluoride, ammonium hydrogenfluoride, tetrabutylammonium fluoride or the like can be used.

The reaction with such a nucleophilic reagent may be carried out by using a nucleophilic reagent in an amount of 2 to 100 moles, preferably 2 to 50 moles for 1 mole of the compound of formula [V], in a glycol solvent such as 2-methoxyethanol or 2,3-butanediol, at a temperature ranging from room temperature to 300° C., preferably from 50 to 200° C.

The compound of formula [VI] thus obtained may be isolated by a conventional means for the isolation and purification of sugar. For instance, it is possible to purify the reaction solution by silica gel column chromatography after it is partitioned between ethyl acetate and water, followed by elution with an organic solvent such as n-hexane/ethyl acetate, thereby isolating the compound [VI].

2nd step:

The 2nd step is a step of selectively deprotecting the isopropylidene group at the 5- and 6-positions of the compound represented by formula [VI], selectively protecting the primary hydroxyl group of the compound, introducing a leaving group into the secondary hydroxyl group of the compound, deprotecting the primary hydroxyl group, performing 5,6-epoxidation, performing 5,6-thiiranation by using a sulfurizing reagent, opening the thiirane ring by using a nucleophilic reagent, and causing acylation, thereby obtaining a compound represented by formula [VII]:

wherein $R_4$ and $R_5$ represent an alkyl or acyl group.

The selective deprotection of the isopropylidene group at the 5- and 6-positions may be achieved by a conventional technique of acid hydrolysis. Examples of acids that can be used in the acid hydrolysis include mineral acids such as hydrochloric acid and sulfuric acid, and organic acids such as acetic acid, trifluoroacetic acid and p-toluenesulfonic acid. When the deprotection reaction is carried out, an acid to be used is diluted with water to a proper concentration, and, when necessary, the diluted acid is mixed with an organic solvent such as THF or dioxane to obtain a solvent mixture. The deprotection reaction can be carried out by using such an acid at a temperature of −50 to 150° C., preferably −20 to 100° C., with stirring.

An ordinary hydroxy-protecting group may be used as the protecting group which is used for the selective protection of the primary hydroxyl group. Examples of such a protecting group include benzyl protecting groups such as benzyl and dimethoxybenzyl, silyl protecting groups such as t-butyldimethylsilyl, t-butyldiphenylsilyl and triethylsilyl, ether protecting groups such as methoxymethyl, methoxyethoxyethyl, tetrahydrofuran and tetrahydropyran, trityl protecting groups such as trityl, monomethoxytrityl, dimethoxytrityl, and acyl groups such as acetyl, benzoyl and pivaloyl.

The introduction of such a protecting group may be achieved by a conventional means. For example, in the case where a silyl protecting group such as t-butyldiphenylsilyl group, or an acyl group such as benzoyl group is introduced, the reaction can be carried out by using 0.8 to 10 moles of a silylating agent (e.g., t-butyldiphenylsilyl chloride, or the like) or acylating agent (e.g., benzoyl chloride, or the like), and, when necessary, 1 to 5 moles of a base such as imidazole or pyridine for 1 mole of the compound of formula [VI], in a reaction solvent (e.g., a single solvent or solvent mixture of pyridine, picoline, dimethylaminopyridine, dimethylformamide, acetonitrile, methylene chloride, or the like), at a temperature of −20 to 50° C.

Further, as the leaving group to be introduced into the secondary hydroxyl group, the same leaving groups as those enumerated in the 1st step can be used. The introduction of such a leaving group can be effected by the same method as that described in the 1st step.

The deprotection of the primary hydroxyl group may be achieved by a technique properly selected, depending upon the protecting group used, from conventional techniques such as acid hydrolysis, alkali hydrolysis combined with ester interchange, a treatment with a fluoride, and catalytic hydrogenation. In particular, when alkali hydrolysis and ester interchange are performed, epoxidation reaction also proceeds simultaneously under the same conditions. However, when the epoxidation reaction proceeded merely insufficiently under the conditions of the alkali hydrolysis and ester interchange, or when the deprotection was conducted under other conditions, the cis-diol derivative obtained by the deprotection can be converted into the desired epoxy derivative by treating the cis-diol derivative with a base. Examples of the bases that can be used in this treatment include sodium hydride, potassium hydride, butyl lithium, lithium diisopropylamide, sodium methoxide, sodium ethoxide, potassium carbonate, and sodium carbonate. The treatment with such a base can be carried out by using 0.5 to 5 moles of a base for 1 mole of the compound of formula [IV], in an organic solvent such as an ether solvent, for instance, ether, THF or dioxane, or an alcohol solvent, for instance, methanol or ethanol, at a temperature of −50 to 120° C.

The conversion of the epoxidized derivative obtained into a thuiirane derivative can be effected by using 0.1 to 10 moles of a sulfurizing reagent for 1 mole of the compound of formula [VI], in an organic solvent such as an alcohol solvent (for example, methanol, ethanol or isopropano), pyridine, acetonitrile or DMF, at a temperature of 0 to 150° C. Examples of sulfurizing reagents that can be used in the above treatment include thiourea, xanthate and thiocarbonyl diimidazole.

The ring opening of the thiirane derivative obtained, and the introduction of an acyl group can be effected by using 1 to 100 moles of an organic acid, organic acid salt or acid anhydride for 1 mole of the compound of formula [VI], in any mixture of organic acids, organic acid salts and acid anhydrides, at a temperature ranging from room temperature to 200° C. Examples of organic acids that can be used in the above reaction include acetic acid, propionic acid, benzoic acid, pivalic acid and trifluoroacetic acid; examples of organic acid salts include sodium acetate, potassium acetate, lithium acetate, sodium propionate, potassium propionate, lithium propionate, sodium benzoate, potassium benzoate, lithium benzoate, sodium trifluoroacetate, potassium trifluoroacetate and lithium trifluoroacetate; and examples of acid anhydrides include acetic anhydride, propionic anhydride, benzoic anhydride, pivalic anhydride and trifluoroacetic anhydride.

The compound of formula [VII] thus obtained may be isolated by a conventional means for the isolation and purification of sugar. For instance, it is possible to purify the reaction solution by silica gel column chromatography after it is partitioned between ethyl acetate and water, followed by elution with an organic solvent such as n-hexane/ethyl acetate, thereby isolating the compound [VII].

3rd step:

The 3rd step is a step of hydrolyzing the isopropylidene group at the 1- and 2-positions of the compound represented by formula [VII], carrying out oxidation by using an oxidizing agent, alkoxylating the 1-position, and protecting the hydroxyl group with a protecting group, thereby obtaining a compound represented by formula [VIII]:

wherein $R_4$ and $R_5$ are as defined before, $R_6$ and $R_7$ represent an alkyl or acyl group, and $R_8$ represents an alkyl group.

The hydrolysis of the isopropylidene group at the 1- and 2-positions can be carried out by the same method as that used for the deprotection of the isopropylidene group at the 5- and 6-positions, described in the above 2nd step.

The oxidation can be carried out by using 0.1 to 10 moles of an oxidizing agent such as sodium periodate or potassium permanganate for 1 mole of the compound of formula [VII], in a single solvent of an organic solvent such as an alcohol solvent (for example, methanol), an ether solvent (for example, THF or dioxane), methylene chloride, dichloroethane, benzene or toluene, or in a solvent mixture of such a solvent with water, at a temperature of −50 to 100° C., preferably −20 to 50° C.

The alkoxylation reaction of the 1-position can be effected by using largely excessive hydrogen chloride, in an alcohol solvent such as methanol, ethanol, isopropanol, t-butanol or benzyl alcohol, at a temperature of −50 to 100° C.

An ordinary hydroxy-protecting group may be used as the protecting group for the hydroxyl groups at the 3- and 5-positions. Examples of such a protecting group include benzyl protecting groups such as benzyl and dimethoxybenzyl, silyl protecting groups such as t-butyldimethylsilyl, t-butyldiphenylsilyl and triethylsilyl, ether protecting groups such as methoxymethyl, methoxyethoxyethyl, tetrahydrofuran and tetrahydropyran, trityl protecting groups such as trityl, monomethoxytrityl and dimethoxytrityl, and acyl groups such as acetyl, benzoyl and pivaloyl. The introduction of a protecting group can be achieved by the same method as that described in the above 2nd step.

The compound of formula [VIII] thus obtained may be isolated by a conventional means for the isolation and purification of sugar. For example, it is possible to purify the reaction solution by silica gel column chromatography after it is partitioned between ethyl acetate and water, followed by elution with an organic solvent such as n-hexane/ethyl acetate, thereby isolating the compound [VIII].

4th step:

The 4th step is a step of brominating the alkoxy group at the 1-position of the compound represented by formula [VIII] by treating the compound [VIII] with a hydrogen bromide/acetic acid solution, subjecting the brominated compound and activated cytosine to glycosylation reaction to obtain a protected compound, removing the protecting groups, and, if desired, phosphorylating the 5'-position of the sugar moiety of the compound, thereby obtaining a 1-(2-deoxy-2-fluoro-4-thio-beta-D-arabinofuranosyl)cytosine represented by formula [I]:

wherein $R_6$, $R_7$ and $R_8$ are as defined before, and R represents a hydrogen atom or a phosphoric acid residue.

The bromination of the alkoxy group at the 1-position of the compound of formula [VIII] can be effected by treating the compound with a hydrogen bromide-acetic acid solution containing approximately 0.1 to 10 moles of hydrogen bromide for 1 mole of the compound of formula [VIII], with or without a solvent mixture with methylene chloride, chloroform, dichloroethane or the like, at a temperature of −50 to 70° C.

Further, in the case where the above bromination reaction does not fully proceed, it is possible to firstly decompose the compound of formula [VIII] by adding acetic acid to obtain a 1-acetoxy derivative, which may then be subjected to the above-described bromination reaction. The decomposition of the compound of formula [VIII] with the addition of acetic acid is effected in a mixture of acetic acid and acetic anhydride in an amount of 1 mole to a largely excessive amount for 1 mole of the compound of formula [VIII], in the presence of a mineral acid such as sulfuric acid, at a temperature of −20 to 100° C., preferably 0 to 50° C.

The glycosylation reaction can be carried out by using 1 to 10 moles of activated cytosine (silylated cytosine, or a metallic salt or alkyl ammonium salt of cytosine), and, when necessary, 0.1 to 10 moles of a Lewis acid such as trimethylsilyl trifluoromethanesulfonate, tin tetrachloride, titanium tetrachloride, zinc chloride or boron trifluoride for 1 mole of the compound of formula [VIII], in a reaction solvent such as methylene chloride, chloroform, dichloroethane, acetonitrile, dimethylformamide or the like, at a temperature of −50 to 100° C., under a stream of an inert gas such as argon or nitrogen.

Alternatively, it is also possible to carry out the glycosylation reaction in an organic solvent such as methylene chloride, chloroform, dichloroethane or acetonitrile, or in the absence of a solvent, in the presence of silylated cytosine, and, when necessary, a catalyst such as sodium iodide, at a temperature ranging from room temperature to 200° C.

The protecting group may be removed by a technique properly selected, depending upon the protecting group used, from conventional techniques such as acid hydrolysis, alkali hydrolysis, a treatment with a fluoride, and catalytic hydrogenation. In particular, in the case where a benzyl protecting group is removed, it is desirable to employ a method in which deprotection is achieved by using boron trichloride or boron tribromide in methylene chloride at a temperature ranging from −100° C. to room temperature under a stream of an inert gas such as argon or nitrogen.

Further, when a compound of formula [I] in which R is a phosphoric acid residue is synthesized, the desired compound of free acid type or salt type can be obtained by a conventional method, e.g., by reacting the compound which has been produced and deprotected by the above method with a phosphorylating agent used for a conventional reaction for selectively phosphorylating the 5'-position of nucleosides, such as phosphorus oxychloride, tetrachloropyrophosphoric acid or beta-cyanoethylphosphoric aciDCC.

The compound of the present invention thus obtained can be isolated and purified by a technique which is a proper combination of techniques conventionally used for the isolation and purification of nucleosides or nucleotides. For instance, in the case of the isolation of a nucleoside derivative (where R in formula [I] is a hydrogen atom), the desired compound may be obtained by crystallization from a proper solvent such as ethanol, which is carried out after the solvent in the reaction solution is distilled off. The desired compound can also be obtained as a salt-type compound, if necessary. Further, in the case of the isolation of a nucleotide derivative (where R in formula [I] is a phosphoric acid residue), the reaction solution may be purified by ion-exchange column chromatography, or adsorption column chromatography using activated carbon or the like, and then freeze-dried or crystallized to obtain the desired compound of free acid type. If necessary, the desired compound can also be obtained as a salt-type compound.

(3) Use of the Compounds of the Invention

The compounds of the present invention have excellent antitumor activity as shown in Test Examples, which will be described later. Therefore, the compositions of the present invention comprising these compounds as active ingredients are useful in the treatment of malignant tumors (e.g., lung cancer, carcinoma of the esophagus, gastric cancer, colonic cancer, rectal cancer, pancreatic carcinoma, breast cancer, cancer of the kidney, bladder carcinoma, carcinoma uteri, osteosarcoma and melanoma).

The dose of the compounds of the present invention varies depending upon the age and body weight of the recipient, the disease, the severity of the condition of the recipient, the permissibility, and the route for administration; and it is to be properly decided by taking all of these factors into consideration. In general, however, the dose is selected from the range of 0.001 to 1,000 mg per kilogram body weight, preferably from the range of 0.01 to 100 mg per kilogram body weight. The desired dose is administered at one time. Alternatively, the desired dose is divided into sub-doses, and the sub-doses are administered several times per day.

The compounds can be administered via any route; they can be administered orally, parenterally, rectally or topically. When the compounds of the present invention are made into formulations, carriers, excipients and other additives which are usually used for conventional formulations can be used. Examples of the carriers include solid carriers such as lactose, kaolin, sucrose, crystalline cellulose, corn starch, talc, agar, pectin, stearic acid, magnesium stearate, lecithin and sodium chloride, and liquid carriers such as glycerin, peanut oil, polyvinyl pyrrolidone, olive oil, ethanol, benzyl alcohol, propylene glycol and water.

The formulations may be presented in any form. For instance, when a solid carrier is used, the form includes tablet, powder, granule, capsule, suppository and troche; and, when a liquid carrier is used, the form includes syrup, emulsion, soft gelatin capsule, cream, gel, paste, spray and injection.

EXAMPLES

The present invention will now be specifically explained by referring to the following Synthesis Examples, Test Examples and Formulation Examples. However, the present invention is not limited by these examples in any way.

Synthesis Example 1

Synthesis of 1-(2-deoxy-2-fluoro-4-thio-beta-D-arabinofuranosyl)cytosine (R=H in formula [I])

(1) Synthesis of 1,4-anhydro-5-O-t-butyldiphenylsilyl-3-O-benzyl-2-deoxy-2-fluoro-4-thio-D-arabitol ($R_1$=Bn and $R_2$=TBDPS in formula [III])

37.7 g of 1,4-anhydro-3-O-benzyl-4-thio-D-arabitol ($R_1$=Bn in formula [II]) and 11.3 g of imidazole were dissolved in 400 ml of DMF. To this solution was added 42.9 ml of t-butyldiphenylsilyl chloride (TBDPSCl) with ice-cooling, and the mixture was stirred at 0° C. overnight under a stream of argon. Water was added to the mixture, and the resulting mixture was stirred at room temperature for a while. Thereafter, the solvent was distilled off, and the residue was partitioned between ethyl acetate and water. The organic layer was further washed with water, and dried. The solvent was concentrated, and the residue was purified by silica gel column chromatography. The fractions eluted with 2–10% ethyl acetate/n-hexane were concentrated to obtain 53.4 g (yield 71%) of the 5-silyl derivative.

5.06 g of the 5-silyl derivative was dissolved in 25 ml of methylene chloride. To this solution, 25 ml of a methylene chloride solution containing 2.26 ml of diethylaminosulfur trifluoride (DAST) was added dropwise at −78° C. under a stream of argon, and the mixture was stirred at −78° C. for 3 hours. The reaction was terminated by adding a saturated aqueous solution of sodium hydrogencarbonate, and the reaction solution was extracted with chloroform. The organic layer was dried over anhydrous sodium sulfate, and the solvent was distilled off. The residue was purified by silica gel column chromatography. The fractions eluted with 2–4% ethyl acetate/n-hexane were concentrated to obtain 2.78 g (yield 55%) of the desired product.

$^1$H-NMR (CDCl$_3$) δ 7.71–7.63 (4H, m, C$_6$H$_5$) 7.71–7.63 (11H, m, C$_6$H$_5$), 5.18 (1H, d q, H-2, J=3.5, 50.5 Hz), 4.64 (1H, d, C$_6$H$_5$CH$_2$, J=12.0 Hz), 4.60 (1H, d, C$_6$H$_5$CH$_2$, J=12.0 Hz), 4.35 (1H, dt, H-3, J=2.9, 11.2 Hz), 3.76 (1H, t, H-5a, J=9.5 Hz), 3.66 (1H, ddd, H-5b, J=2.0, 6.1, 10.5 Hz), 3.57–3.53 (1H, m, H-4) 3.19 (1H, ddd, H-1a, J=4.4, 12.2, 30.3 Hz) 3.06 (1H, ddd, H-1b, J=3.4, 12.2, 18.1 Hz), 1.05 (9H, s, tBu)

(2) Synthesis of 1-O-acetyl-5-O-t-butyldiphenylsilyl-3-O-benzyl-2-deoxy-2-fluoro-4-thio-D-arabinose ($R_1$=Bn, $R_2$=TBDPS and $R_3$=Ac in formula [IV])

2.58 g of the 1,4-anhydro-5-O-t-butyldiphenylsilyl-3-O-benzyl-2-deoxy-2-fluoro-4-thio-D-arabitol was dissolved in 15 ml of methylene chloride, and the solution was cooled to −78° C. under a stream of argon. To this solution, a solution of 1.15 g of 80% m-chloroperbenzoic acid in methylene chloride was added dropwise, and the mixture was stirred for 30 minutes. Thereafter, the reaction was terminated by adding a saturated sodium hydrogencarbonate solution. The reaction solution was allowed to warm up to room temperature, and extracted with chloroform. The organic layer was dried, and the solvent was distilled off. The residue was dissolved in 30 ml of acetic anhydride, and the temperature of the solution was maintained at 110° C. for 2 hours under a stream of argon. After the solution was cooled to room temperature, the solvent was distilled off under reduced pressure. The residue was dissolved in ethyl acetate, and the solution was partitioned among water, a saturated aqueous solution of sodium hydrogencarbonate, and a saturated saline solution, and then dried over anhydrous sodium sulfate. The solution was concentrated under reduced pressure, and the residue was purified by silica gel column chromatography. The fractions eluted with 5–10% ethyl acetate/n-hexane were concentrated to obtain 1.57 g (yield 54%) of the desired product.

$^1$H-NMR (CDCl$_3$) δ 7.68–7.62 (4H, m, C$_6$H$_5$) 7.46–7.25 (11H, m, C$_6$H$_5$) 6.06 (1H, d, H-1, J=4.4 Hz), 5.11 (1H, ddd, H-2, J=4.4, 8.3, 51.0 Hz), 4.78 (1H, d, C$_6$H$_5$CH$_2$, J=11.7 Hz), 4.60 (1H, d, C$_6$H$_5$CH$_2$, J=11.7 Hz), 4.38 (1H, ddd, H-3, J=7.3, 8.3, 11.7 Hz), 3.81 (1H, dd, H-5a, J=4.4, 10.5 Hz), 3.74 (1H, dd, H-5b, J=5.9, 10.5 Hz), 3.34 (1H, ddd, H-4, J=4.4, 5.9, 7.3 Hz), 2.05 (3H, s, Ac), 1.07 (9H, s, tBu)

(3) Synthesis of 1-(2-deoxy-2-fluoro-4-thio-beta-D-arabinofuranosyl) cytosine (R=H in formula [I])

971 mg of the 1-O-acetyl-5-O-t-butyldiphenylsilyl-3-O-benzyl- 2-deoxy-2-fluoro-4-thio-D-arabinose was dissolved in 20 ml of acetonitrile. To this solution were added silylated N$^4$-acetylcytosine (prepared by heating 832 mg of N$^4$-acetylcytosine and a catalytic amount of ammonium sulfate in hexamethyldisilazane for 5 hours under reflux), and 3.60 ml of a solution of 1M tin tetrachloride in methylene chloride and the mixture was stirred at room temperature for 3 hours. To this mixture was further added 1.80 ml of a solution of 1M tin tetrachloride in methylene chloride. The resulting mixture was stirred at room temperature for 1 hour, and a saturated sodium hydrogencarbonate solution was then added thereto. The mixture was filtered through Celite to remove insolubles, and extracted three times with chloroform. The organic layer was dried. The filtrate was concentrated under reduced pressure, and the residue was purified by silica gel column chromatography. The fractions eluted with 1% methanol/n-chloroform were collected, and concentrated to obtain 672 mg (yield 59%) of the desired protected product.

614 mg of the protected product was dissolved in 15 ml of methylene chloride. To this solution, 4.85 ml of 1 M trichloroboran was added dropwise at −78° C. under a stream of argon. The temperature of the mixture was raised to 0° C., and the mixture was stirred for 30 minutes. To this mixture were added 2 ml of pyridine and 5 ml of methanol. The resulting mixture was stirred at −78° C. for a further 30 minutes, and then allowed to warm up to room temperature. The solvent was distilled off, and the residue was azeotropically distilled three times with methanol. The solvent was then distilled off, and the residue was dissolved in 10 ml of methanol. To this solution was added 360 mg of ammonium fluoride, and the temperature of the mixture was maintained at 60° C. for 2 hours. The mixture was then concentrated under reduced pressure. To the resultant were added 15 ml of methanol and 15 ml of concentrated aqueous ammonia, and the mixture was stirred at room temperature overnight. The solvent was distilled off, and the residue was azeotropically distilled with ethanol. The residue was successively purified by silica gel column chromatography and ODS reverse phase column chromatography to obtain 29 mg of the title compound.

$^1$H-NMR (DMSO-d$_6$) δ 7.98 (1H, dd, H-6, J=1.0, 7.2 Hz) 7.26, 7.19 (2H, br, NH$_2$) 6.47 (1H, dd, H-1, J=5.4, 13.2 Hz) 5.85 (1H, d, 3-OH, J=4.9 Hz), 5.77 (1H, d, H-5, J=7.3 Hz), 5.22 (1H, t, 5-OH, J=5.4 Hz), 4.91 (1H, dt, H-2', J=5.4, 50.8 Hz), 4.25 (1H, ddt, H-3', J=4.9, 5.4, 11.2 Hz), 3.72 (1H, dt, H-5'a, J=5.4, 11.2 Hz), 3.60 (1H, dt, H-5'b, J=5.9, 11.2 Hz), 3.22 (1H, dt, H-4', J=5.4, 5.9 Hz)

Synthesis Example 2

Synthesis of 1-(2-deoxy-2-fluoro-4-thio-beta-D-arabinofuranosyl)cytosine (R=H in formula [I])

(1) Synthesis of 1,2:5,6-di-O-isopropylidene-3-deoxy-3-fluoro-alpha-D-glucofuranose (formula [VI])

20.0 g (76.84 mmol) of 1,2:5,6-di-O-isopropylidenealpha-D-allofuranose (formula [V]) was dissolved in 240 ml of CH$_2$Cl$_2$. To this solution was added dropwise 12.35 ml (153.68 mmol) of SO$_2$Cl$_2$ at 0° C., and the mixture was stirred for 15 minutes. Thereafter, 52.3 g (768.40 mmol) of imidazole was slowly added to the mixture with ice-cooling, and the resulting mixture was stirred at room temperature for 2 to 3 hours. After the reaction was terminated by adding saturated NaHCO$_3$, the reaction solution was extracted with CHCl$_3$. The organic layer was dried over Na$_2$SO$_4$, and the solvent was distilled off. The residue was dissolved in 240 ml of 2-methoxyethanol. To this solution was added 44.64 g (768.40 mmol) of potassium fluoride (spray-dried product), and the mixture was heated under reflux at 130° C. for 4 to 6 hours. After the mixture was allowed to cool, the solvent was distilled off, and the residue was partitioned between ethyl acetate and water. The organic layer was successively washed with H$_2$O×2 and brine, dried over Na$_2$SO$_4$, and then evaporated to dryness under reduced pressure. Purification by column chromatography on silica gel (400 cc, 5–20% AcOEt (in hexane)) gave 12.98 g (49.49 mmol) of the desired product in a yield of 64%.

$^1$H-NMR (CDCl$_3$) δ 5.95 (d, 1H, H-1, J$_{1,2}$=3.9 Hz), 5.01 (dd, 1H, H-3, J$_{3,4}$=2.2 Hz, J$_{3,F}$=49.8 Hz), 4.70 (dd, H, H-2, J$_{1,2}$=3.9 Hz, J$_{2,F}$=10.7 Hz), 4.2 9 (1H, ddd, H-5, J$_{4,5}$=8.3 Hz, J$_{5,6a}$=5.9 Hz, J$_{5,6b}$=4.9 Hz), 4.12 (dd, 1H, H-6a, J$_{5,6a}$=5.9 Hz, J$_{6a,b}$=8.8 Hz), 4.11 (ddd, 1H, H-4, J$_{3,4}$=2.2 Hz, J$_{4,5}$=8.3 Hz , J$_{4,F}$=29.0 Hz), 4.03 (dd, 1H, H-6b, J$_{5,6}$=4.9 Hz, J$_{6a,b}$= 8.8 Hz) 1.50, 1.45, 1.37, 1.33 (s, each 3H, ipr)

(2) Synthesis of 5,6-di-S,O-acetyl-1,2-O-isopropylidene-5-thio-alpha-D-glucofuranose (R$_4$=R$_5$=Ac in formula [VII])

10.9 g (41.56 mmol) of 1,2:5,6-di-O-isopropylidene-3-deoxy-3-fluoro-alpha-D-glucofuranose was dissolved in 40 ml of THF and 40 ml of 2 N HCl, and the solution was stirred at room temperature. After the reaction was completed, the reaction solution was neutralized with NaHCO$_3$, and the resultant was filtered to remove insolubles. The filtrate was extracted with CHCl$_3$. The organic layer was washed with brine, and dried over Na$_2$SO$_4$. The solvent was distilled off, and the residue was purified by column chromatography on silica gel (320 cc, 3–6% MeOH (in CHCl$_3$)) to obtain 8.02 g (36.09 mmol) of 1,2-O-isopropylidene-3-deoxy-3-fluoro-alpha-D-glucofuranose. 1,2-O-Isopropylidene-3-deoxy-3-fluoroalpha-D-glucofuranose was dissolved in 120 ml of $CH_2Cl_2$. 3.20 ml of pyridine and 44 mg of DMAP were added to the solution. To this mixture was added dropwise a solution of 4.61 ml (39.68 mmol) of BzCl in 50 ml of $CH_2Cl_2$ at −5° C. Reaction was carried out at −5° C. for 5 hours. After the completion of the reaction was confirmed, MeOH was added to the reaction solution, and the mixture was stirred for 1 hour to terminate the reaction. The resultant was partitioned between $CHCl_3$ and $H_2O$. The organic layer was successively washed with 0.5 N HCl×2, saturated $NaHCO_3$×2, and brine, and then dried over $Na_2SO_4$. The solvent was distilled off, and the residue was purified by column chromatography on silica gel (320 cc, 10–25% AcOEt (in hexane)) to obtain 9.33 g (28.59 mmol) of 6-O-benzoyl-1,2-O-isopropylidene-3-deoxy-3-fluoro-alpha-D-glucofuranose in a yield of 79%.

$^1$H-NMR ($CDCl_3$) δ ppm 8.09–8.05 (m, 2H, Bz) 7.60–7.42 (m, 3H, Bz), 5.99 (d, 1H, H-1, $J_{1,2}$=3.9 Hz), 5.14 (dd, 1H, H-3, $J_{3,4}$=2.0 Hz, $J_{3,F}$=49.8 Hz), 4.74–4.70 (m, 2H, H-2, H-6a) 4.46 (dd, 1H, H-6b, $J_{5,6b}$=5.9 Hz, $J_{6a,b}$=12.2 Hz 4.27–4.18 (m, 2H, H-4, $H_5$), 2.8 3 (br, 1H, 5-OH), 1.47, 1.33 (s, each 3H, ipr)

9.33 g (28.59 mmol) of 6-O-benzoyl-1,2-O-isopropylidene-3-deoxy-3-fluoro-alpha-D-glucofuranose was dissolved in 80 ml of pyridine. To this solution was added dropwise 3.32 ml (42.88 mmol) of MsCl at 0° C. and the mixture was stirred at room temperature overnight. The reaction was terminated by adding $H_2O$ at 0° C. and the reaction solution was extracted with ethyl acetate. The organic layer was washed with saturated $NaHCO_3$ and brine, and then dried over $Na_2SO_4$. The solvent was distilled off. To the residue were successively added 80 ml of MeOH and 7 ml (34.31 mmol) of 28% $NaOCH_3$. The mixture was stirred at room temperature for 45 minutes, and then partitioned between ethyl acetate and water. The organic layer was dried over $Na_2SO_4$, and purified by column chromatography on silica gel (220 cc, AcOEt:hexane=(5:1) to (1:1)) to obtain 3.82 g (65%) of 5,6-anhydro-1,2-O-isopropylidene-3-deoxy-3-fluoro-alpha-L-idofuranose, and 1.404 g (16) of 1,2-O-isopropylidene-3-deoxy-3-fluoro-5-O-methanesulfonyl-alpha-D-glucofuranose. 1,2-O-Isopropylidene-3-deoxy-3-fluoro-5-O-methanesulfonyl-alpha-D-glucofuranose was dissolved in 10 ml of THF, and treated with 206 mg (5.14 mmol) of 60% NaH to convert it into 5,6-anhydro-1,2-O-isopropylidene-3-deoxy-3-fluoro-alpha-L-idofuranose.

$^1$H-NMR ($CDCl_3$) δ ppm 6.04 (d, 1H, H-1, $J_{1,2}$=3.9 Hz), 4.96 (dd, 1H, H-3, $J_{3,4}$=2.4 Hz, $J_{3,F}$=50.3 Hz), 4.71 (dd, 1H, H-2, $J_{1,2}$=3.9 Hz, $J_{2,F}$=11.2 Hz), 3.89 (ddd, 1H, H-4, $J_{3,4}$=2.4 Hz, $J_{4,5}$=5.9, $J_{4,F}$=30.3 Hz), 3.22 (1H, ddd, H-5, $J_{4,5}$=5.9 Hz, $J_{5,6a}$=4.4 Hz, $J_{5,6b}$=2.9 Hz ), 2.88 (t, 1H, H-6a, J=4.4 Hz), 2.71 (dd, 1H, H-6b, $J_{5,6b}$=2.9 Hz, $J_{6a,b}$=4.9 Hz), 1.47, 1.33 (s, each 3H, ipr)

3.82 g (18.7 mmol) of 5,6-anhydro-1,2-O-isopropylidene-3-deoxy-3-fluoro-alpha-L-idofuranose was dissolved in 90 ml of MeOH. To this solution was added 1.42 g (18.7 mmol) of thiourea, and the mixture was heated under reflux for 7 hours. After the mixture was allowed to cool, the solvent was distilled off. The residue was partitioned between $H_2O$ and $CHCl_3$, and the organic layer was dried over $Na_2SO_4$. The solvent was distilled off to obtain, as a residue (3.99 g), 5,6-anhydro-1,2-O-isopropylidene-3-deoxy-3-fluoro-5-thio-alpha-D-glucofuranose. Further, from 5,6-anhydro-1,2-O-isopropylidene-3-deoxy-3-fluoro-alpha-L-idofuranose (crude) which was obtained by treating 1,2-O-isopropylidene-3-deoxy-3-fluoro-5-O-methanesulfonyl-alpha-D-glucofuranose with NaH, 5,6-anhydro-1,2-O-isopropylidene-3-deoxy-3-fluoro-5-thio-alpha-D-glucofuranose was obtained as a residue (0.87 g) in the same manner as the above. The combined residues were dissolved in a mixture of 15 ml of AcOH and 75 ml of $Ac_2O$. To this solution was added 3.46 g (35.29 mmol) of potassium acetate, and the mixture was heated under reflux for 20 hours. After the mixture was allowed to cool, the solvent was distilled off. The residue was suspended in ethyl acetate, and the suspension was filtered to remove insolubles. The filtrate was sequentially washed with $H_2O$×2, saturated $NaHCO_3$ and brine, dried over $Na_2SO_4$, and evaporated to dryness under reduced pressure. The residue was purified by column chromatography on silica gel (220 cc, 15–20% AcOEt (in hexane)). Thus, 5.2 g (16.13 mmol) of 5,6-di-S,O-acetyl-1,2-O-isopropylidene-5-thio-alpha-D-glucofuranose was obtained in a yield of 73%.

Melting Point: 88.9–90.4° C.; Elemental Analysis (for $C_{13}H_{19}O_6SF$); Calculated C: 48.44; H: 5.94; Found C: 48.49; H: 6.00; $^1$H-NMR ($CDCl_3$) δ ppm 5.98 (d, 1H, H-1, $J_{1,2}$=3.9 Hz), 4.96 (dd, 1H, H-3, $J_{3,F}$=49.6 Hz), 4.68 (dd, 1H, H-2, $J_{1,2}$=3.9 Hz), 4.46–4.37 (m, 3H, H-6a, H-6b, H-4), 4.11 (dt, 1H, H-5), 2.36 (s, 3H, Ac) 2.06 (s, 3H, Ac), 1.49 (s, 3H, ipr), 1.33 (s, 3H, ipr)

(3) Synthesis of methyl 3,5-di-O-benzoyl-2-deoxy-2-fluoro-4-thio-D-arabinofuranose ($R_6$=$R_7$=Bz and $R_8$=Me in formula [VIII])

100 mg (0.31 mmol) of 5,6-di-S,O-acetyl-1,2-O-isopropylidene-5-thio-alpha-D-glucofuranose was dissolved in 90% trifluoroacetic acid (1.5 ml). The solution was stirred at 0° C. for 4 hours, and then diluted with ethyl acetate. The organic layer was sequentially washed with $H_2O$×3, saturated $NaHCO_3$×2 and brine, and dried over $Na_2SO_4$. The solvent was distilled off, and the residue was dissolved in 0.8 ml of MeOH. To this solution was added 0.8 ml of an aqueous solution of 58.4 mg (0.27 mmol) of $NaIO_4$ at room temperature. After the reaction was completed, glycerin was added to the reaction solution, and the mixture was stirred for 30 minutes to terminate the reaction. Insolubles were removed by filtration. The filtrate was evaporated to dryness under reduced pressure, and the residue was partitioned between $H_2O$×3 and $CHCl_3$. The organic layer was washed with brine, and dried over $Na_2SO_4$. The solvent was distilled off, and the residue was dissolved in 2 ml of 5% HCl/MeOH. The solution was heated under reflux for 4 hours, and then neutralized with $NaHCO_3$. Insolubles were filtered off, and the solvent was distilled off. The residue was dissolved in 2 ml of pyridine. To this solution was added 150 microlitters (1.29 mmol) of BzCl at 0° C., and the mixture was stirred at room temperature for 2.5 hours. The reaction was terminated by adding saturated $NaHCO_3$, and the reaction solution was extracted with $CHCl_3$. The organic layer was successively washed with 0.5 N HCl, saturated $NaHCO_3$ and brine, dried over $Na_2SO_4$, and evaporated to dryness under reduced pressure. The residue was purified by flash column chromatography on silica gel (15 cc, 5% AcOEt (in hexane)). Thus, 28 mg of the alpha-anomer, 24.5 mg of the beta-anomer, and 13.1 mg of a mixture of the alpha- and beta-anomers were respectively obtained (total 54%). (alpha-anomer)

1H-NMR ($CDCl_3$) δ ppm 8.03–7.99 (4H, m, Bz) 7.60–7.35 (6H, m, Bz), 5.77 (1H, dt, H-1) 5.28 (1H, dd, H-2, $J_{2,F}$=8.3 Hz), 5.24 (1H, d, H-3, $J_{2,3}$=2.0 Hz), 4.61–4.47 (2H, m, H-5a, 5b), 4.05 (1H, dt, H-4), 3.42 (3H, s, OMe) (beta-anomer) $^1$H-NMR ($CDCl_3$) δ ppm 8.04–8.02 (4H. m, Bz), 7.59–7.31 (6H, m, Bz) 6.09 (1H, dt, H-1, $J_{1,2}$=3.9 Hz), 5.35 (1H, ddd, H-2. $J_{2,F}$=51.5 Hz) 4.96 (1H, d, H-3), 4.57

(2H, ddd, H-5a, 5b. $J_{5a,b}$=11.2 Hz, $J_{5a,4}$=$J_{4,5b}$=6.4 Hz), 3.69 (1H, dt, H-4, $J_{4,5a}$=$J_{4,5b}$=6.4 Hz), 3.43 (3H, s, OMe)

(4) 1-(2-deoxy-2-fluoro-4-thio-beta-D-arabinofuranosyl) cytosine (R=H in formula [I])

24.2 mg (0.062 mmol) of methyl 3,5-di-O-benzoyl-2-deoxy-2-fluoro-4-thio-alpha- and -beta-D-arabinofuranose was dissolved in a mixture of 2 ml of AcOH and 2 ml of $Ac_2O$. To this solution was added 0.25 ml of conc. sulfuric acid at 0° C., and the mixture was stirred at room temperature for 1 hour. The mixture was neutralized with 4.5 g of NaOAc, and then partitioned between $CH_2Cl_2$ and $H_2O$. The organic layer was dried over $Na_2SO_4$. The solvent was distilled off, and the residue was purified by column chromatography on silica gel (10 cc, 10% AcOEt (in hexane)). Thus, 23.5 mg (0.056 mmol) of 1-O-acetyl-3,5-di-O-benzoyl-2-deoxy-2-fluoro-4-thio-D-arabinofuranose was obtained as a mixture of the alpha- and beta-anomers in a yield of 91%.

$^1$H-NMR ($CDCl_3$) δ ppm 8.06–7.94 (m, 4H, Bz) 7.62–7.30 (m, 6H, Bz), 6.24 (dd, 0.42H, H-1a, $J_{1,2}$=2.0 Hz, $J_{1,F}$=14.2 Hz), 6.18 (d, 0.58H, H-1β, $J_{1,2}$=4.4 Hz), 6.08 (ddd, 0.58H, H-3β, $J_{3,4}$=7.3 Hz, $J_{2,3}$=9.3 Hz, $J_{3,F}$=11.7 Hz), 5.85 (dt, 0.42H, H-3α, $J_{2,3}$=$J_{3,4}$=3.9 Hz, $J_{3,F}$=12.2 Hz), 5.39 (ddd, 0.42H, H-2α, $J_{1,2}$=2.0 Hz, $J_{2,3}$3.9 Hz, $J_{2,F}$=47.9 Hz), 5.31 (ddd 0.58H, H-2β, $J_{1,2}$=4.4 Hz, $J_{2,3}$=9.3 Hz, $J_{2,F}$=50.8 Hz), 4.69 (dd, 0.58H, H-5βa, $J_{4,5a}$=6.4 Hz , $J_{5a,b}$=11.2 Hz), 4.55 (dd, 0.42H. H-5αa, $J_{4,5a}$=7.8 Hz. $J_{5a,b}$=11.7 Hz), 4.49 (dd, 0.58H, $H_5$βb, $J_{4,5b}$=6.4, $J_{5a,b}$=11.2 Hz 4.47 (dd, 0.42H, H-5αb, $J_{4,5b}$=1.5 Hz, $J_{5a,b}$=11.7 Hz) 4.11 (ddd, 0.42H, H-4α, $J_{3,4}$=4.4 Hz, $J_{4,5}$=7.8 Hz, $J_{4,5b}$=1.5 Hz), 3.74 (q, 0.58H, H-4β, $J_{3,4}$=$J_{4,5a}$=$J_{4,5b}$=6.4 Hz), 2.12, 2.11 (s, total 3H, Ac)

150 mg (0.358 mmol) of 1-O-acetyl-3,5-di-O-benzoyl-2-deoxy-2-fluoro-4-thio-D-arabinofuranose was dissolved in 1.5 ml of $CH_2Cl_2$. To this solution was added 0.3 ml of 30% HBr/aetic acid, and the mixture was stirred at room temperature for 20 minutes. The reaction was terminated by adding 15 ml of ice water, and the reaction solution was extracted with $CH_2Cl_2$. The organic layer was washed with saturated $NaHCO_3$ and ice water, dried over $Na_2SO_4$, and then evaporated to dryness at a temperature of 30° C. or lower under reduced pressure to obtain the 1-bromo derivative as an oil. This 1-bromo derivative was added to silylated acetylcytosine [prepared by dissolving 82.3 mg (0.538 mmol) of acetylcytosine in 2.5 ml of dichloroethane, adding 267 microliters (1.08 mmol) of BSA to the solution, heating the mixture under reflux for 3 hours, and concentrating the reaction solution to dryness], and glycosylation was performed at 80° C. for 5 hours under a reduced pressure of 4 mmHg or lower. The resulting product was suspended in $CHCl_3$, and the unreacted base was filtered off. The filtrate was concentrated. The concentrate was dissolved in a mixture of 3 ml of MeOH and 3 ml of $NH_4OH$, and the solution was stirred overnight. The solvent was distilled off, and the residue was purified by flash column chromatography on silica gel (20 cc, $CHCl_3$:MeOH (10:1) to (3:1)). Thus, 59.3 mg (0.227 mmol) of 1-(2-deoxy-2-fluoro-4-thio-beta-D-arabinofuranosyl)-cytosine was obtained as a mixture of the alpha- and beta-anomers in a yield of 63.4%. The beta/alpha ratio determined by HPLC (YMC A-312, 275 nm, 5% $CH_3CN$ (in 50 mM TEAA)) was 5.02. This mixture was separated into the beta-anomer and the alpha-anomer in the same manner as in Synthesis Example 1

Test Example 1

Inhibitory Activity of Proliferation of Cultured Cell (in vitro test)

(Method)

10 microlitters of a sample solution or a Hanks' MEM was placed on a 96-well plate. Cells in the logarithmic growth phase were diluted with an RPMI 1640 medium to which 10% of fetal calf serum had been added, and then inoculated on the plate so that the number of the cells would be 5,000/90 microliters/well. This was incubated in a $CO_2$-incubator at 37° C. for 3 days. After the incubation was completed, 10 microlitters of an MTT solution (5 mg/ml (in PBS)) was added to each well, and incubation was conducted in the $CO_2$-incubator at 37° C. for a further 4 hours. After the incubation was completed, 100 microlitters of 0.02 N hydrochloric acid/50% dimethylformamide/20% SDS was added to each well, and the formazane produced was dissolved by stirring. The absorbance at 570 nm (test wavelength) or at 690 nm (control wavelength) was measured by a microplate reader ("Toso MPR 4Ai"). The 50% inhibitory concentration ($ID_{50}$) of the sample was calculated by the probit method, using a computer soft.

In the above test, the test sample was dissolved in dimethyl sulfoxide so that the concentration thereof would be 10 mg/ml; the solution was preserved at 4° C., and then diluted with a Hanks' MEM; and the resultant was used therein.

(Results)

The results of the test carried out by using the compound of the present invention are shown in Table 1. In the table, "CCRF-HSB-2" indicates human leukemia cell, "KB" indicates cancer cell of the human rhinopharynx, and "MKN-45" and "MKN-28" indicate human gastric cancer cell.

TABLE 1

| | $IC_{50}$ (μg/ml) | | | |
|---|---|---|---|---|
| Compound | CCRF-HSB-2 | KB | MKN-45 | MKN-28 |
| Compound of the Invention | 0.051 | 0.015 | 2.1 | 0.027 |
| Ara-C | 0.052 | 0.26 | >20 | 0.36 |

Test Example 2

In Vivo Antitumor Activity on Murine Sarcoma S-180

(Method)

Mouse sarcoma S-180 cells were intraperitoneally subinoculated in ICR mice. 6 or 7 days after the transplantation, abdomen-swollen mice were selected, and abdominal dropsy was collected therefrom. The abdominal dropsy collected was diluted with sterile PBS so that the number of the cells would be $5\times10^7$/ml. The cell suspension thus prepared was subcutaneously transplanted to the flanks of female ICR mice of 5 weeks old in an amount of 0.1 ml ($5\times10^6$ cells) per mouse. A sample was dissolved in a physiological saline solution (PSS). The resulting solution was intravenously administered to the mice in an amount of 0.1 ml per 10 g body weight once a day for 10 days from the 3rd day after the transplantation. On the other hand, the vehicle (PSS) was administered to the mice in the control group.

4 weeks after the transplantation, the tumors were removed from the mice, and weighed. The antitumor activity was evaluated by comparing the weights of the tumors removed from the mice in the sample administration group with those of the tumors removed from the mice in the control group.

(Results)
The results of the measurement are shown in Table 2.

TABLE 2

| Compound | Dose (mg/kg) | Schedule of Administration | Weight of Tumor (average ± standard deviation) | T/C (%) |
| --- | --- | --- | --- | --- |
| Control | — | Day 3–12 | 8.20 ± 2.84 | 100 |
| Compound of the Invention | 30 | Day 3–5, 8–12 | 2.09 ± 1.44 | 25 |
|  | 10 | Day 3–12 | 2.20 ± 0.94 | 27 |
|  | 3 | Day 3–12 | 1.36 ± 0.90 | 17 |
|  | 1 | Day 3–12 | 5.34 ± 4.11 | 65 |
| Furtulon | 30 | Day 3–12 | 5.57 ± 1.10 | 68 |
|  | 10 | Day 3–12 | 9.22 ± 2.90 | 112 |

Test Example 3
In Vivo Antitumor Effect (1) on Human Colonic Carcinoma SW-48 Cells
(Method)
SW-48 cells were cultured in an RPMI 1640 medium containing 10% of fetal calf serum, harvested in the logarithmic growth phase, and subcutaneously transplanted to the flanks of female BALB/c nude mice of 5 weeks old so that the number of the cells would be $1\times10^7$/mouse. A sample was dissolved in a physiological saline solution (PSS). The resulting solution was intravenously administered to the mice once a day for 10 days (qd×10) from the 7th day after the transplantation. On the other hand, the vehicle (PSS) was dministered to the mice in the control group.

Figure 1:
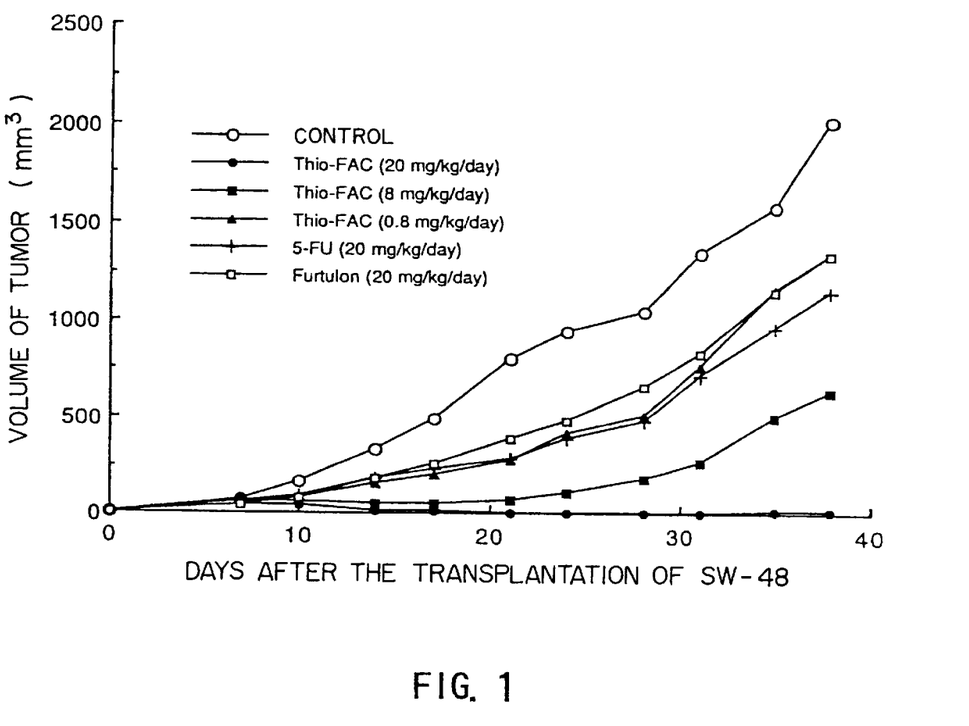
FIG. 1 is a graph showing the in vivo antitumor effect of the compound of the present invention on the human colonic carcinoma SW-48 cells, obtainable when the compound is administered intravenously.

The sizes of -the tumors of the mice were measured twice a week, and the volumes of the tumors were obtained by calculation from the following formula. The antitumor effect was evaluated by comparing the growth curve of the tumors of the mice in the sample administration group with that of the tumors of the mice in the control group.

$$V=(L\times W^2)/2$$

wherein V: the volume of tumor ($mm^3$),
L: the length of tumor (mm), and
W: the width of tumor (mm).
(Results)
The results of the measurement are shown in FIG. 1. In this figure, "Thio-FAC" indicates the compound of the present invention, and "5-FU" indicates 5-fluorouracil.

Test Example 4
In Vivo Antitumor Effect (2) on Human Colonic Carcinoma SW-48 Cells
(Method)
SW-48 cells were cultured in an RPMI 1640 medium containing 10% of fetal calf serum, harvested in the logarithmic growth phase, and subcutaneously transplanted to the flanks of female BALB/c nude mice of 5 weeks old so that the number of the cells would be $1\times10^7$/mouse. sample was dissolved or suspended in a physiological saline solution (PSS) containing 0.5% carboxymethyl cellulose. The resulting solution or suspension was orally administered to the mice once a day for the consecutive 10 days, or every three days four times in all, from the 7th day after the transplantation. On the other hand, the vehicle (PSS used above) was administered to the mice in the control group.

Figure 2:
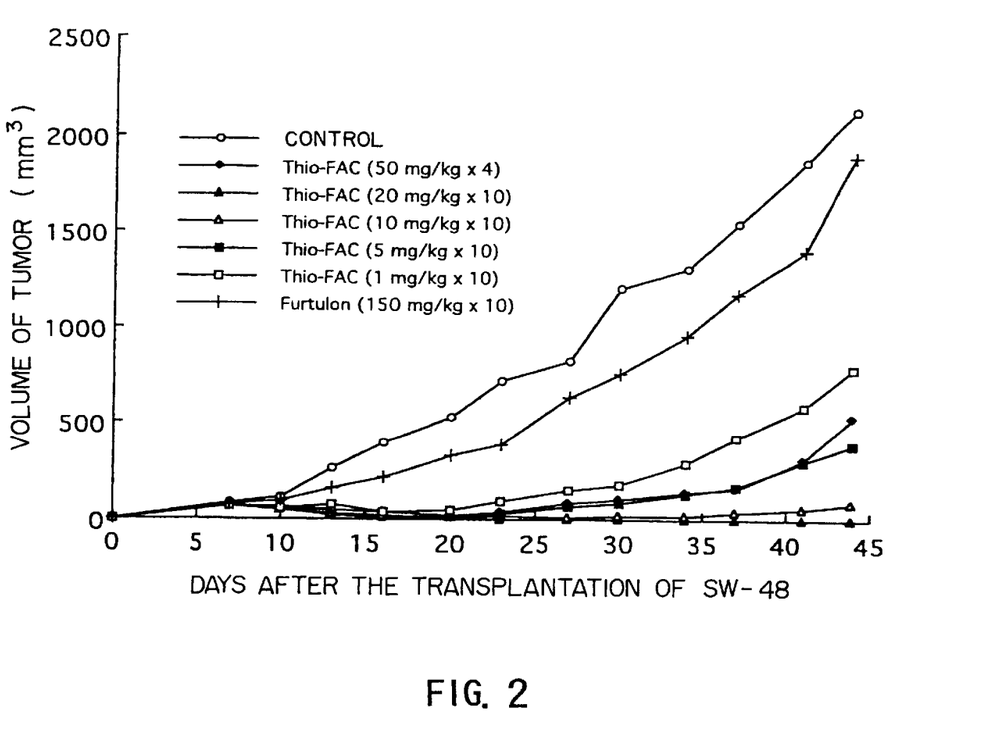
FIG. 2 is a graph showing the in vivo antitumor effect of the compound of the present invention on the human colonic carcinoma SW-48 cells, obtainable when the compound is administered orally.

The sizes of the tumors of the mice were measured twice a week, and the volumes of the tumors were obtained by calculation from the above formula. The antitumor effect was evaluated by comparing the growth curve of the tumors of the mice in the sample administration group with that of the tumors of the mice in the control group.
(Results)
The results of the measurement are shown in FIG. 2. In this figure, "Thio-FAC" indicates the compound of the present invention.

Formulation Example 1: Tablet

| Compound of the invention | 30.0 mg |
| --- | --- |
| Cellulose fine powder | 25.0 mg |
| Lactose | 39.5 mg |
| Starch | 40.0 mg |
| Talc | 5.0 mg |
| Magnesium stearate | 0.5 mg |

Tablets are prepared by a conventional method according to the above composition.

Formulation Example 2: Capsule Formulation

| Compound of the invention | 30.0 mg |
| --- | --- |
| Lactose | 40.0 mg |
| Starch | 15.0 mg |
| Talc | 5.0 mg |

A capsule formulation is prepared by a conventional method according to the above composition.

Formulation Example 3: Injectable Formulation

| Compound of the invention | 30.0 mg |
| --- | --- |
| Glucose | 100.0 mg |

An injectable formulation is prepared by dissolving the above ingredients in purified water for injections.

INDUSTRIAL APPLICABILITY

The compounds of the present invention have excellent antitumor activity, and are expected to be developed into pharmaceuticals. Further, the production processes of the present invention can be practiced by using inexpensive materials as starting materials with a small number of steps and simple operation, so that they are extremely practical.

We claim:
1. A 1-(2-deoxy-2-fluoro-4-thio-beta-D-arabinofuranosyl)-cytosine represented by formula (I):

(I)

wherein R represents a hydrogen atom or a phosphoric acid residue.

2. A pharmaceutical composition comprising a compound set forth in claim 1 as the active ingredient, and a pharmaceutically acceptable carrier.

3. A method of treating tumors which comprises administering to a patient in need of such treatment, the pharmaceutical composition according to claim 2.

4. A process for producing a compound set forth in claim 1, which comprises:

$1^{st}$ step:

protecting the primary hydroxyl group of compound (II):

(II)

wherein $R_1$ and $R_2$ represent an alkyl, silyl or acyl group;

and then reacting the thus protected compound with diethylaminosulfur trifluoride (DAST) to produce compound (III):

(III)

$2^{nd}$ step:

converting the compound of formula (III) into a sulfoxide by reacting it with an oxidizing agent;

(III)

subjecting the sulfoxide to a Pummerer rearrangement reaction by treating it with an acid anhydride or acid chloride, thereby obtaining a compound represented by formula (IV):

(IV)

wherein $R_1$ and $R_2$ are as defined above, and $R_3$ represents an acyl group; and $3^{rd}$ step:

subjecting the compound represented by formula (IV) and $N^4$-acylcytosine or cytosine to a glycosylation reaction in the presence of a Lewis acid catalyst to obtain a protected compound, (IV)

removing the protecting groups, and, optionally, phosphorylating the 5'-position of the sugar moiety of the compound, thereby obtaining a 1-(2-deoxy-2-fluoro-4-thio-beta-D-arabinofuranosyl)cytosine represented by formula (I):

(I)

wherein $R_1$, $R_2$ and $R_3$ are as defined above, and R represents a hydrogen atom or a phosphoric acid residue;

and recovering compound (I).

5. A process for producing a compound set forth in claim 1, which comprises:

$1^{st}$ step:

a step of introducing a leaving group into the hydroxyl group on a compound represented by formula (V), (1)

(V)

R₉:leaving group and treating the compound with a nucleophilic reagent by which a fluorine atom can be introduced, thereby obtaining a compound represented by formula (VI):

(2)

(VI)

R₉:leaving group

2ⁿᵈ step:
a step of selectively deprotecting the isopropylidene group at the 5- and 6-positions of the compound represented by formula (VI):

(1)

(VI)

selectively protecting the primary hydroxyl group of the compound,

(2)

introducing a leaving group into the secondary hydroxyl group of the compound, (3)

R₉:leaving group deprotecting the primary hydroxyl group and performing 5,6-epoxidation, (4)

R$_9$:leaving group performing 5,6-thiiranation by using a sulfurizing reagent,

(5)

opening the thiirane ring by using a nucleophilic reagent, and causing acylation thereby obtaining a compound represented by formula (VII):

(6)

(VII)

wherein R$_4$ and R$_5$ represent an alkyl or acyl group;

3$^{rd}$ step:

hydrolyzing isopropylidene group at the 1- and 2-positions of the compound represented by formula (VII), (1)

(VII)

carrying out oxidation by using an oxidizing agent,

(2)

alkoxylating the 1-position,

(3)

and protecting the hydroxyl group with a protecting group, thereby obtaining a compound represented by formula (VIII):

(4)

(VIII)

wherein $R_4$ and $R_5$ are defined as above, $R_6$ and $R_7$ represent an alkyl or acyl group, and $R_8$ represents an alkyl group; and

$4^{th}$ step:

brominating the alkoxy group at the 1-position of the compound represented by formula (VIII) by treating the compound (VIII) with a hydrogen bromide-acetic acid solution,

(VIII)

subjecting the brominated compound and activated cytosine to glycosylation reaction to obtain a protected compound, removing the protecting groups, and optionally, phosphorylating the 5'-position of the sugar moiety of the compound, thereby obtaining a 1-(2-deoxy-2-fluoro-4-thio-beta-D-arabinofuranosyl)cytosine represented by formula (I):

(I)

wherein $R_6$, $R_7$, and $R_8$ are as defined above, and R represents a hydrogen atom or a phosphoric acid residue, and recovering compound (I).

* * * * *